United States Patent [19]

Loshaek

[11] E Patent Number: Re. 33,477

[45] Reissued Date of Patent: Dec. 4, 1990

[54] ULTRAVIOLET ABSORBING HYDROPHILIC CORNEAL CONTACT LENSES

[75] Inventor: Samuel Loshaek, Chicago, Ill.

[73] Assignee: Wesley-Jessen, Inc., Chicago, Ill.

[21] Appl. No.: 369,241

[22] Filed: Jun. 20, 1989

Related U.S. Patent Documents

Reissue of:

[64] Patent No.: 4,304,895
Issued: Dec. 8, 1981
Appl. No.: 741,695
Filed: Nov. 15, 1976

U.S. Applications:

[62] Division of Ser. No. 371,603, Jun. 20, 1973, abandoned.

[51] Int. Cl.[5] ..... C02C 7/04; C08F 12/24; C08F 16/12; C08F 216/12

[52] U.S. Cl. ..... 526/313; 264/1.1; 351/160 H; 523/106; 524/558; 526/316

[58] Field of Search ..... 526/313, 316; 523/106; 524/558

[56] References Cited

U.S. PATENT DOCUMENTS

| | | | |
|---|---|---|---|
| 3,171,869 | 3/1965 | Weinberg | 264/1 |
| 3,173,893 | 3/1965 | Fertig et al. | 526/313 |
| 4,304,895 | 12/1981 | Loshaek | 523/106 |
| 4,390,676 | 6/1983 | Loshaek | 526/313 |

OTHER PUBLICATIONS

UVC Brochure (Guaranteed Plastic Lenses), undated document.

Fertig Article (Journal of Applied Polymer Science), vol. 10, pp. 663–672.

*Primary Examiner*—Harold D. Anderson

*Attorney, Agent, or Firm*—Poms, Smith, Lande & Rose

[57] ABSTRACT

This invention relates to ultraviolet absorbing lenses, particularly corneal contact lenses, comprising a polymeric shaped body having an ultraviolet absorber dispersed substantially uniformly throughout said body and being in a steady state with respect to extraction thereof from said body by an aqueous medium, and to the method of making such lenses.

4 Claims, No Drawings

ULTRAVIOLET ABSORBING HYDROPHILIC CORNEAL CONTACT LENSES

Matter enclosed in heavy brackets [ ] appears in the original patent but forms no part of this reissue specification; matter printed in italics indicates the additions made by reissue.

This is a division, of application Ser. No. 371,603, filed June 20, 1973, now abandoned.

BACKGROUND OF THE INVENTION

Many who have had the natural lens of the eye damaged as by injury or by disease require surgery resulting in removal of the natural lens. This condition of lens removal is known as aphakia and must be corrected by the use of a high plus corrective lens in order to restore vision.

Such corrective lenses may be in the form of spectacles or contact lenses, but contact lenses are preferred since spectacles are not only cosmetically undesirable because of their thickness to provide the correct vision, but in addition produce an excessively large image on the retina. Even with the most suitable lenses, including contact lenses, presently in use, vision is not as desirable as it should be for the aphakic individual since such lenses do not adequately compensate for certain changes in light transmission which occur in the absence of the natural human crystalline lens. The result is a lack of visual acuity and high chromatic aberration in aphakic individuals.

A considerable portion of incident light entering the eye is absorbed by various parts of the eye, as described herein, so that only the unabsorbed or transmitted portion strikes the retina. The incident light is, of course, comprised of the entire spectrum of wavelengths including the ultraviolet, visible and infrared.

Specifically, the cornea preferentially absorbs that portion of the light with wavelengths up to about 340 mmu. The crystalline lens preferentially absorbs the wavelengths from about 340 up to about 400 mmu. There is also a characteristic absorption of the visible portion of the spectrum by various parts of the eye. The overall result of the various absorptions in the human eye is to permit the unabsorbed light to be transmitted to the retina, this light being defined by wavelength and intensity at each wavelength. It is apparent that in the aphakic eye, where there is no crystalline lens, light from 340 to 400 mmu will be transmitted to the retina and that absorption in the visible range of the spectrum will also be changed to the extent that such visible light was absorbed by the crystalline lens. In other words, the spectrum of the light striking the retina in the aphakic eye is different from that in the normal eye.

SUMMARY OF THE INVENTION

Suitable lenses have now been found which restore the normal elements of vision for aphakic individuals.

Briefly stated, the present invention comprises an ultraviolet absorbing lens comprising a polymeric shaped body having an ultraviolet absorber dispersed substantially uniformly throughout said body, said absorber being selected from an ultraviolet absorber capable of absorbing radiation in the wavelength range of about 340 to 450 mmu (i.e., 3400 to 4500 A) and an ultraviolet absorber present in an amount such that it is capable of absorbing radiation in the wavelength of about 340 to 450 mmu, and said absorber having reached a steady state as defined herein with respect to extraction thereof from said body by an aqueous medium and to the method of making such lens. A preferred embodiment is directed to corneal contact lenses in which the ultraviolet absorber is a polymerizable material copolymerized with the monomeric material used to form the lens.

DETAILED DESCRIPTION

While the present invention is applicable to contact lenses and to lenses to be used in spectacles, it will be described in connection with corneal contact lenses.

The essential requirements of the present invention are that the ultraviolet absorbing polymer, from which the lens is fabricated, provides the required light absorption spectrum and that the absorbing component not be extracted in amounts which might adversely affect the eye. The absorbing components are aromatic chemical compounds which may be irritants to the eye or may have adverse effects if permitted to come in contact with the eye over a long period of time, such as that approaching the useful life of the lens. The preferred lens polymer is one that gives zero extractible of the ultraviolet absorbing component, however, polymers which give very low extractibles such as, for example, less than one part of absorbing component per million parts of lens per day are also satisfactory. It has been found for the polymers of this invention that the extraction of freshly fabricated lenses give an initially greater amount of extractibles over some finite period of time, followed eventually by a significantly lower amount of extractibles. As an approximation, this extraction pattern can be expressed in terms of rates of extraction. The lower rate which is eventually reached is usually extremely low and approximately constant. This latter rate is referred to as the steady state rate. It is possible, that with some of the polymers of this inverntion, the rate of extraction may be zero from the outset, thus the steady state rate is zero for this case. It will be seen from the examples that the steady state rate is reached at different times for different polymers.

It is also possible that the lens has not reached the steady state with respect to extractibles as the time that it is put into use. Through extraction by the eye fluid and by contact lens solutions in which the lenses are stored, extraction will occur and the steady state reached at some time after the lens has been put into use. It is preferred but not essential to have the lens at steady state with regard to extraction prior to putting it into use, by means of an extraction procedure such as described later herein.

The ultraviolet absorbing lenses of the present invention are, therefore, those which are capable of being brought into a steady state condition with regard to extractibles in an aqueous medium (including isotonic saline and tears) in a finite period of time. Where an extraction procedure is used prior to putting the lens in service, the extraction may be carried out in any suitable non-solvent for the polymer, such as water, saline, aliphatic hydrocarbons (such as pentene, hexane, heptane, and the like), and like extractants. The condition of steady state extractibility is, however, defined in terms of an aqueous medium, isotonic saline, tears, etc. The extraction time required to put the lens into the steady state should advantageously be as short as possible, with times of zero to seven days being preferred.

As to materials, the lens itself is a polymeric shaped body formed by polymerizing any of the monomeric materials used to make such lenses, whether the lens be of the "hard" type or the hydrophilic type ("soft" lens). Examples of suitable materials that can be used to form the lens are the silicone polymers and polymers comprising monomers, such as methyl methacrylate, hydroxyethyl methacrylate, ethyleneglycol dimethacrylate and mixtures thereof and the like. The particular monomer, or combination of monomers, as well as other additives, such as cross-linking agents and polymerization catalysts, used to form the polymeric lens form no part of the instant invention in that any known in the lens art can be used and in the proportions conventionally used for making lenses.

As to the ultraviolet absorber, it must be capable of absorbing radiation in the wavelength range of about 340–450 mmu and preferably one which absorbs it above about 375 mmu and permits less than 50% and preferably less than about 30% transmission at 400 mmu. It is possible to obtain such transmission characteristics with use of known ultraviolet absorbers having the noted wavelength transmissions or by varying the concentration of known absorbers to give such absorption characteristics.

The absorbers are preferably monomeric materials that can be copolymerized with the monomeric materials forming the shaped lens body. As described more fully later herein, this minimizes the problem of extractible materials in the lens.

Specific examples of the non-polymerizable absorbers are 2,2'-dihydroxy-4,4'-dimethoxy-benzophenone; 2,2'-dihydroxy-4-methoxy-benzophenone; 2,2'-dihydroxy-4-n-octyloxy-benzophenone and mixtures thereof. Other ultraviolet materials that can be used can be selected from the known ultraviolet absorbing materials having the capacity to absorb the wavelength transmissions necessary.

Examples of suitable copolymerizable monomer ultraviolet absorbers are

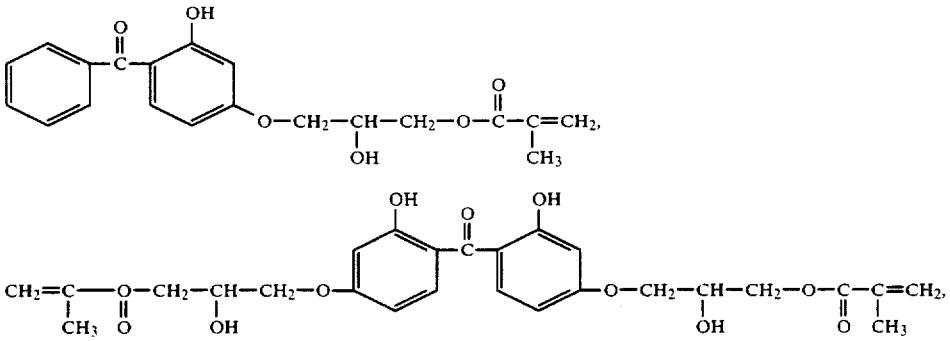

(Compound I)

2-hydroxy-4-methacryloxy benzophenone and mixtures thereof. Here, again other polymerizable monomers having the necessary ultraviolet transmission absorption characteristics may be utilized. Copolymerizable monomeric ultraviolet absorbing monomers are broadly described in U.S. Pat. No. 3,162,676 and British Pat. No. 885,986.

In the present invention, if a hydrophilic lens is to be made, then it is preferred to use a polymerizable ultraviolet absorber as this will not be leached out by virtue of the hydrophilic nature of the polymer forming the shaped body. The hydrophilic polymer permits absorption and elution of ingredients thereby permitting any material disposed in the lens and not part of the polymer makeup of the lens to be removed from the lens.

In addition to the essential and critical components of the lens discussed above, it is preferred to also add visible light absorbers for selectively absorbing wavelengths in the visible region. Such absorbers are included in order to limit transmission of a minor percentage of visible light through the lens and onto the retina. Absent such visible light absorptions, excessive brightness can result in an aphakic individual leading to uncomfortable vision and poorer color perception. The usual light absorbing dyes can be used for this purpose with an orange color seemingly giving the best results.

As to proportions, the maximum amount of ultraviolet absorber added to the lens is less than 5% and preferably less that 3% by weight of the monomers used to form the lens. With the polymerizable ultraviolet absorbers larger concentrations of absorber can be used since they will not be extracted from the lens. The amount of visible light absorber added can be that required to give the degree of light absorption desired and can vary widely, although it is desired that visible light transmission not be reduced below about 70% of the total light. Ordinarily, the amount comprises less than about 0.01 part by weight for each 100 parts by weight of the lens.

In preparing the lens, it is required that the ultraviolet absorber and dye, if such is to be added, be added to the mixture of monomers and other materials used to form the lens. Some initial admixing is required in order to insure the thorough dispersal of the absorbers throughout the polymerized body of the lens. Ordinarily, contact lenses are formed by polymerizing the materials in a tube until the polymerization is complete. The result is a rod which is then sliced into discs and the discs converted into contact lenses by the machining procedures conventional to the contact lens art and which form no part of the instant invention.

It is a feature of the instant invention, however, to further treat the lens by extraction at room or high temperatures up to about 170° F. for a sufficient period of time to bring the ultraviolet absorber to a steady state. The extraction temperature should not exceed that at which the contact lens would be distorted. The extraction is preferably carried out in water or 0.9% aqueous saline at 40° C., which temperature approximates the human eye fluid temperature of about 37.5° C. The extraction may also be carried out in a non-aqueous medium which is a non-solvent for the polymer at the desired temperature. Aliphatic hydrocarbon solvents, of which hexane is an example, can be used. The extracting solvent and temperature of extraction should be such as not to distort the part being extracted. It is preferred to extract the lens in a state where it is as near to the final form as possible. One advantageous point of extraction is at the point where the entire contact lens has been fabricated except for the outside peripheral curve. The extracted lens can then be stored in inventory and the final curve applied when a definite prescription is received. If the lens is made to order to a known prescription, the extraction is preferably carried out after the entire lens has been fabricated. The attainment of a steady state is determined by analyzing aliquots of the extracting solution for its concentration of extracted ultraviolet absorber in a spectrophotometer and comparing the extent of absorption at the characteristic absorption maxima for the absorber against a calibration curve. It will be obvious that once a standard formulation for a lens is determined, then the time required to reach a steady state for any such given formulation can be standardized based on the type of extracting solution and temperature used. When polymerizable ultraviolet absorbers are used, their incorporation in the polymer forming the lens substantially reduces or eliminates the need for extraction as noted previously. Thus, a steady state for the absorber with respect to extraction can be attained by actually extracting the lens or by using a polymerizable absorber.

The invention will be further described in connection with the following examples which are set forth for purposes of illustration only and in which proportions are by weight unless specifically stated to the contrary.

EXAMPLE 1

A corneal contact lens was prepared from the following formulation:

| | Parts by Weight |
|---|---|
| Methyl methacrylate | 95 |
| Ethyleneglycol dimethacrylate | 5 |
| Bisazoisobutyronitrile | 0.2 |
| 2,2'-dihydroxy-4,4'-dimethoxy-benzophenone (UV absorber) | 0.1 |
| D&C Red #17 | 0.002 |
| D&C Yellow #11 | 0.004 |

All the components of the formulation were mixed and the mixture poured into glass test tubes of about ¾ inch diameter. The tubes were then placed in an 80° F. bath until the mixture solidified (approximately 3 days). The test tubes were then transferred to an oven and subjected to increasing temperatures reaching a maximum of 105° C. in 3 days. The test tubes were then removed from the oven, allowed to reach room temperature, and the glass broken leaving polymerized plastic rods. Plastic discs about ¼ inch in thickness were sliced off the rods and the discs converted into corneal contact lenses having a center thickness of 0.02 inches, outside diameter of 10 mms. base curve radius of 8 mms. and 0.045 gram average weight using conventional contact lens making equipment.

The transmission spectrum of the lenses was determined on a UV spectrophotometer. Extraction of the lenses was usually carried out by placing six lenses in a screw cap vial containing 6 mls of extracting medium and placing the vial in the desired temperature environment. To accentuate extractibility, tests were also conducted on lathe turnings of the polymer resulting from machining of the polymer rods. In these experiments usually 0.5 gram of turnings was added to the screw cap vial containing 10 ml. of extracting fluid and the results were calculated in terms of the extractible UV absorber from 0.045 grams of turnings. The extracting medium was analyzed for its concentration of extracted ultraviolet absorber by placing a 1 cc. aliquot in the spectrophotometer and comparing the extent of absorption of the characteristic absorption maxima for the absorber against a calibration curve. The wavelength, steady state, and extraction results are set forth in Table I.

EXAMPLES 2–14

A series of corneal contact lenses was prepared and tested as set forth in Example 1, except that different ultraviolet absorbers and/or proportions thereof were used in place of the absorber used in Example 1. In addition, in Example 13, no visible light absorbing dyes were used and, in Example 14, D&C Green #6 was substituted for the dyes used in Example 1.

The test results are set forth in Table I.

TABLE I

| Example No. | UV Absorber | Concentration Parts/100 Parts Monomer | Polymerizable | Cut-off Wavelength[1] (mmu) | % Transmission[2] at 400 (mmu) | Days to Steady State Extraction at Ambient Temp.[3] | Micrograms Extracted at Start of Steady State and (Steady State Extraction Rate[4] of UV Absorber): mcgm per lens per day | mcgm per ml. per .045 gms turnings/day |
|---|---|---|---|---|---|---|---|---|
| 1 | 2,2'-dihydroxy-4,4' dimethoxy-benzophenone | 0.1 | No | 370 | 30 | 17–20 | 0.045 (0.00016) | 0.117 (0.0014) |
| 2 | 2,2'-dihydroxy-4,4' dimethoxy benzophenone | 0.5 | No | 385 | 10 | 20 | 0.160 (0.00070) | 0.630 (0.0051) |
| 3 | 2,2'-dihydroxy-4-methoxy-benzophenone | 0.1 | No | 360 | 43 | 16 | N.A. | Extracted 0.09 at 16 days, 40° C. |
| 4 | 2,2'-dihydroxy-4-η-octyloxy-benzophenone | 0.1 | No | 360 | 41 | 16 | N.A. | N.A. |
| 5 | Compound I | 1.0 | Yes | 360 | 44 | Extracted 4 days at 70° C. and 3 days at Room Temp.[5] | N.A. | 0.57 see footnote[5] |
| 6 | Compound I | 3.0 | Yes | 365 | 36 | Extracted 4 days at 70° C. and 3 days at | N.A. | 0.52 see footnote[5] |

TABLE I-continued

| Example No. | UV Absorber | Concentration Parts/100 Parts Monomer | Polymerizable | Cut-off Wavelength[1] (mmu) | % Transmission[2] at 400 (mmu) | Days to Steady State Extraction at Ambient Temp.[3] | Micrograms Extracted at Start of Steady State and (Steady State Extraction Rate[4] of UV Absorber) mcgm per lens per day | mcgm per ml. per .045 gms turnings/day |
|---|---|---|---|---|---|---|---|---|
| 7 | 2,2'-dihydroxy-4,4'-dimethoxy benzophenone | 0.5 | No | 385 | 10 | Room Temp.[5] Extracted 1 day at 70° C. and 3 days at R.T. | 0.304 see footnote[5] | 0.99 see footnote[5] |
| 8 | Compound II | 0.55 | Yes | 380 | 26 | 4 (40° C.) | N.A. | 0.0180 (0.0019–40° C.) |
| 9 | Compound II | 0.40 | Yes | 375 | 28 | 3–4 (40° C.) | N.A. | 0.0288 (0.0017–40° C.) |
| 10 | Compound II | 0.8 | Yes | 380 | 17 | 4 (40° C.) | N.A. (0.00040–40° C.) | 0.0279 (0.00162–40° C.) |
| 11 | Compound II | 1.0 | Yes | 390 | 13 | | | |
| Human Lens | — | — | — | 388 | 5 | — | — | — |
| 12 | 2-hydroxy-4-methacryloxy benzophenone | 0.6 | Yes | 340 | 46 | N.A. | N.A. | N.A. |
| 13 | 2,2'-dihydroxy-4,4' dimethoxy- | 0.5 | No | 390 | 22 | 17–20 | 0.20 (0.0008) | 0.53 (0.0075) |
| 14 | 2,2'-dihydroxy-4,4' dimethoxy-benzophenone | 0.5 | No | 390 | 22 | 17–20 | 0.20 (0.008) | 0.50 (0.0072) |

[1]Determined on a 0.020 inch thick lens. Cut-Off Wavelength is that at which the transmission reached 0%.
[2]Extractant is a 0.9% aqueous saline solution. Extraction at room temperature.
[3]Temperatures other than room temperature are noted in parentheses. Steady state means that the rate of extraction is constant.
[4]Tests were preformed on groups of 6 lenses with 6 ml. of extracting medium or on 0.5 gram of lathe turnings with 10 ml. of extracting medium or both.
[5]Days to steady state not available; numbers shown are at the end of the indicated treatment.

Other ultraviolet absorbers than shown in the above examples may be used provided they give cut-offs in the range of about 340–450 mmu with the preferred cut-off being above about 375 mmu and the transmission at 400 mmu should be in the range of less than about 50%, with the preferred range being less than about 30%. These cut-off and transmission characteristics simulate that of the human lens, whose characteristics are shown in Table I. The cut-off and transmission characteristics of a particular ultraviolet absorber can be varied to some extent by varying its concentration as can be seen by comparing Examples 1 and 2 and Examples 5 and 6.

Higher levels of polymerizable ultraviolet absorber can be used without as large a concomitant increase in extractibles as would be obtained with the non-polymerizable absorbers. This is illustrated by comparison of Examples 2 and 5 which shows a lower extractible in the latter (0.57 mcgm) as compared to the former (0.63 mcgm) even though the concentration of absorber is greater and the extraction conditions are more severe in Example 5. It is further illustrated by comparing Examples 2 and 9 for extractions from lathe turnings.

The methyl methacrylate monomer in the above examples may be partially replaced with comonomers to provide special physical attributes, e.g., ethylene glycol dimethacrylate as a cross-linking comonomer tends to produce a harder and more stable plastic. The exact nature of this monomer is not a part of this invention but generally the methacrylates are preferred for contact lens manufacture because of their optical qualities. Similarly, the polymerization catalyst bisazoisobutyronitrile may be replaced with any suitable free radical catalyst or combinations thereof such as benzoyl peroxide, isopropyl peroxy dicarbonate, t-butyl perbenzoate, etc. These catalyst are also not a part of the subject invention.

The dyes in Examples 1 to 11 have been chosen to provide a transmission curve in the visible region of the spectrum which simulates that of the human lens. The concentration of the dyes may be varied depending on the desired percent of light transmission, but usually this transmission should be 70% or more for good vision. The chemical structure of these dyes may be different than those demonstrated here provided they perform the same purpose. The use of dyes is preferred but is not essential. To illustrate this point, an aphakic patient was fitted with the lens made from a polymer such as in Example 2 with visible light-screening dyes and another lens made from polymer as in Example 13 with no visible light-screening dyes and a lens made from ordinary clear polymethyl methacrylate. The visual acuity, comfort and color perception of the patient in bright daylight was best with the lens from Example 2. With the lens from Example 13, glare was reduced and visual acuity was better than the ordinary lens without ultraviolet absorber, but not as good as with the lens of Example 2. The lens made from ordinary polymethyl methacrylate did not provide any improvement in visual acuity or comfort or improvement in color perception. Thus, the presence of ultraviolet absorber is essential to restore natural vision, especially color vision to the aphakic patient and in combination with a visible dye provides further improvements in these qualities.

EXAMPLE 15

The methyl methacrylate monomer of Example 11 is replaced with an equal weight of hydroxyethyl methacrylate, and without any other changes polymer and contact lenses prepared. This produces a hydrophilic copolymer comprising the ultraviolet absorber in the polymer chains. The ultraviolet absorption at 400 mmu is 15%, the cut-off wavelength is 385 mmu and the extractible characteristics are very similar to those from Example 11. Because of the hydrophilic nature of the polymer which permits absorption and elution of ingredients, it would have been expected that the ultraviolet absorber would be substantially removed by leaching. However, by interpolymerizing the ultraviolet absorber, the ultraviolet absorber is not leached out to any substantial extent.

It is evident that the hydroxyethyl methacrylate may be partially or wholly replaced with other monomers while still retaining a hydrophilic ultraviolet absorbing material on polymerization. Also, the other ingredients may be varied as with the non-hydrophilic examples without departing from the scope of this invention.

EXAMPLE 16

Lenses are prepared as in Example 11 except that the dyes are omitted. The test results will be essentially identical to that set forth for Example 11.

EXAMPLE 17

Lenses are prepared as in Example 11 except that they are extracted with aliphatic hydrocarbons which are non-aqueous and non-solvents for the polymers forming the lenses. Extraction to a steady state is obtained.

The importance of reaching a steady state is to avoid any ultraviolet absorption variables when the lens is placed in the eye of the user where it will be bathed in the normal eye fluids. Thus, the optimum absorption characteristics can be designed into a lens without fear that exposure to eye fluids (as in the case of contact lenses) or cleansing solutions (as in the case of spectacles) with adversely alter such absorption characteristics.

While the invention has been described in connection with a preferred embodiment, it is not intended to limit the invention to the particular form set forth, but, on the contrary, it is intended to cover such alternatives, modifications and equivalents as may be included within the spirit and scope of the invention as defined by the appended claims.

What is claimed is:

1. A corneal contact lens comprising a shaped body comprising a *hydrophilic* polymer formed by copolymerizing a monomer suitable for use in making such lenses and a copolymerizable monomeric ultraviolet absorber, said absorber being in a steady state with respect to extraction thereof from said body by an aqueous medium and being present in an amount sufficient to absorb radiation in the wavelength range of about 340 to 450 mmu.

2. The corneal contact lens of claim 1 wherein the copolymerizable monomeric ultraviolet absorber is selected from:

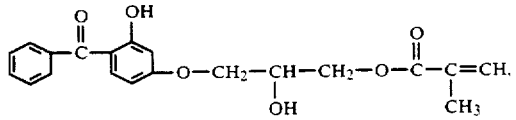

2-hydroxy-4-methacryloxy-benzophenone or mixtures thereof.

3. A corneal contact lens comprising a shaped body comprising a *hydrophilic* polymer formed by copolymerizing a mixture comprising methyl methacrylate, ethyleneglycol dimethacrylate, and a compound of the formula

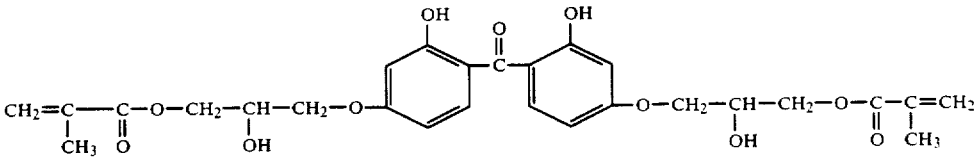

said compound being in a steady state with respect to extraction thereof from said body by an aqueous medium and being present in an amount sufficient to absorb radiation in the wavelength range of about 340 to 450 mmu.

4. The corneal contact lens of claim 3 further comprising a visible light absorbing dye dispersed substantially uniformly throughout said body in an amount sufficient to absorb not more than about 30% of the visible light passing through the lens.

* * * * *